US010203281B2

(12) United States Patent
Sano et al.

(10) Patent No.: US 10,203,281 B2
(45) Date of Patent: Feb. 12, 2019

(54) TRANSMITTED LIGHT INTENSITY MEASUREMENT UNIT

(71) Applicants: NIPRO CORPORATION, Osaka (JP); HARADA ELECTRONICS INDUSTRY CO., LTD., Hokkaido (JP)

(72) Inventors: Yoshihiko Sano, Osaka (JP); Masahide Harada, Hokkaido (JP)

(73) Assignees: NIPRO CORPORATION, Osaka (JP); HARADA ELECTRONICS INDUSTRY CO., LTD., Hokkaido (JP)

( * ) Notice: Subject to any disclaimer, the term of this patent is extended or adjusted under 35 U.S.C. 154(b) by 0 days.

(21) Appl. No.: 15/577,091

(22) PCT Filed: May 27, 2016

(86) PCT No.: PCT/JP2016/065777
§ 371 (c)(1),
(2) Date: Nov. 27, 2017

(87) PCT Pub. No.: WO2016/194834
PCT Pub. Date: Dec. 8, 2016

(65) Prior Publication Data
US 2018/0180541 A1    Jun. 28, 2018

(30) Foreign Application Priority Data

May 29, 2015   (JP) ................................. 2015-109678

(51) Int. Cl.
*G01N 21/00*    (2006.01)
*G01N 21/59*    (2006.01)
(Continued)

(52) U.S. Cl.
CPC ............. *G01N 21/59* (2013.01); *G01N 21/05* (2013.01); *G01N 33/4915* (2013.01); *G01N 2201/0612* (2013.01); *G01N 2201/0621* (2013.01)

(58) Field of Classification Search
CPC ............... G01N 21/8507; G01N 21/31; G01N 21/0303; G01N 21/59; G01N 21/05
(Continued)

(56) References Cited

U.S. PATENT DOCUMENTS

| 4,747,687 A | 5/1988 | Hoppe et al. | |
|---|---|---|---|
| 2013/0280038 A1* | 10/2013 | Martin | F03B 13/00 415/110 |
| 2016/0069803 A1* | 3/2016 | Sano | G01N 21/534 356/440 |
| 2016/0175143 A1* | 6/2016 | Smith | A61F 9/008 606/4 |

FOREIGN PATENT DOCUMENTS

| EP | 0467805 A1 | 1/1992 |
|---|---|---|
| JP | 59-107241 A | 6/1984 |

(Continued)

OTHER PUBLICATIONS

International Search Report issued by the Japanese Patent Office acting as the International Searching Authority in relation to International Patent Application No. PCT/JP2016/065777 dated Jul. 19, 2016 (3 pages) along with English language translation (2 pages).

(Continued)

*Primary Examiner* — Md M Rahman
(74) *Attorney, Agent, or Firm* — Robert P. Michal, Esq.; Carter, DeLuca, Farrell & Schmidt LLP

(57) ABSTRACT

A transmitted light intensity measurement unit for measuring a concentration of fluid flowing through a duct comprises: a light source for supplying light into the duct from a light supply part on a surface of the duct; a light receiving element for receiving the light, which has been passed from the light supply part through the duct wall and the fluid (Continued)

inside the duct, at a light receiving part located on an opposite side in a diametrical direction of the duct relative to the light supply part, and outputs a signal indicating an intensity of the light; and a light-transmissive member disposed on at least one light path among a light pass between the light source and the light supply part and a light pass between the light receiving element and the light receiving part, abutting and closely contacting the duct wall by an elastic deformation of the duct wall.

6 Claims, 2 Drawing Sheets

(51) Int. Cl.
  *G01N 21/05* (2006.01)
  *G01N 33/49* (2006.01)

(58) Field of Classification Search
  USPC .......................................................... 356/436
  See application file for complete search history.

(56) References Cited

FOREIGN PATENT DOCUMENTS

| | | |
|---|---|---|
| JP | 61-003034 A | 1/1986 |
| JP | 9-264845 A | 10/1997 |
| JP | 2006-234663 A | 9/2006 |
| JP | 2014209063 A | 11/2014 |
| WO | WO-2014/170985 A1 | 10/2014 |

OTHER PUBLICATIONS

Written Opinion issued by the Japanese Patent Office acting as the International Searching Authority in relation to International Patent Application No. PCT/JP2016/065777 dated Jul. 19, 2016 (3 pages).

Extended European Search Report issued by the European Patent Office in relation to European Application No. 16803269.6 dated Nov. 19, 2018 (6 pages).

Japanese Office Action (Notification of Reasons of Refusal) issued by the Japanese Patent Office in relation to Japanese Application No. 2015-109678 dated Nov. 21, 2018 (3 pages) along with English language translation (3 pages).

\* cited by examiner

TRANSMITTED LIGHT INTENSITY MEASUREMENT UNIT

CROSS-REFERENCE TO RELATED APPLICATIONS

This application is a national phase entry under 35 U.S.C. 371 of PCT International Application No. PCT/JP2016/0065777 filed May 27, 2016, which claims priority to Japanese Patent Application No. 2015-109678, filed May 29, 2015, the disclosure of each of these applications is expressly incorporated herein by reference in their entirety.

TECHNICAL FIELD

The present invention relates to a transmitted light intensity measurement unit used in a fluid concentration measuring device which measures a concentration of a fluid flowing through a duct having a light-transmissive and deformable duct wall based on the Beer-Lambert law, for measuring an intensity of a transmitted light passed transversely across the duct.

BACKGROUND ART

A resin tube is well known as the duct having such the duct wall as described above, and an example of conventionally known fluid concentration measuring device which measures a concentration of a fluid such as a blood flowing in the resin tube is described in Patent Document 1. The fluid concentration measuring device described in the Patent Document 1 comprises: a transmitted light intensity measurement unit having a light source which supplies light into the duct from a light supply part on a surface of the duct; and a light receiving element which receives the light, which has been passed from the light supply part through the duct wall and the blood inside the duct, at a light receiving part located on an opposite side in a diametrical direction of the duct relative to the light supply part, and outputs a signal indicating an intensity of the light.

The fluid concentration measuring device described above has, further, a light path distance setting means which sets a plurality of light path distances between the light supply part and the light receiving part; and a fluid concentration output means which, from the light intensity at the light receiving part with regard to each of the plurality of light path distances, obtains a plurality of relational expressions, each of which indicates a relation between the light intensity and a blood concentration when the light from the light supply part is received by the light receiving part over each of the light path distances, based on the Beer-Lambert law, and obtains a concentration of the blood in the resin tube from the light intensity at the light receiving part based on the relational expressions for the plurality of light path distances and outputs the concentration of the blood.

PRIOR ART DOCUMENTS

Patent Documents

Patent Document 1: International Publication Laid-Open No. 2014-170985

SUMMARY OF THE INVENTION

Task to be Solved by the Invention

Inventors of the present invention had progressed studying on the conventional fluid concentration measuring device described above, and as a result of studying, the inventors had found out the point below. That is, in the conventional fluid concentration measuring device, there is a disadvantage of difficulty to obtain an enough quantity of light which is supplied from the light source, transmitted through the resin tube and reached to the light receiving element, because the light attenuates due to scattering etc. between the light supply part on the surface of the duct and the light source and/or between the light receiving part on the surface of the duct and the light receiving element in the transmitted light intensity measurement unit. Therefore, it became clear that there is a possibility of improvement in the transmitted light intensity measurement unit to increase a measuring accuracy.

Thus, an object of the present invention is to advantageously solve the problem of the conventional transmitted light intensity measurement unit and consequently the problem of the conventional fluid concentration measuring device, by enabling the transmitted light intensity measurement unit to obtain an enough quantity of light which is supplied from the light source, transmitted through the duct and reached to the light receiving element, in view of the point described above.

Solution for Task

According to the present invention, to solve the problem described above, a transmitted light intensity measurement unit for measuring an intensity of a transmitted light passed transversely across a duct, used in a fluid concentration measuring device which measures a concentration of a fluid flowing through the duct having a light-transmissive and deformable duct wall, is characterized in that the unit comprises:

a light source for supplying light into the duct from a light supply part on a surface of the duct;

a light receiving element for receiving the light, which has been passed from the light supply part through the duct wall and the fluid inside the duct, at a light receiving part located on an opposite side in a diametrical direction of the duct relative to the light supply part, and outputs a signal indicating an intensity of the light; and a light-transmissive member disposed on at least one light path among a light pass between the light source and the light supply part and a light pass between the light receiving element and the light receiving part, abutting and closely contacting the duct wall by an elastic deformation of the duct wall.

Effect Of The Invention

In such a transmitted light intensity measurement unit according to the present invention, a light-transmissive member is disposed on at least one light path among a light pass between the light source and the light supply part and a light pass between the light receiving element and the light receiving part, and the light-transmissive member abuts and closely contacts the duct wall, so that substantially no air layer intermediate between the duct wall and the light-transmissive member, and a surface of the duct wall is made smooth by crushing microscopical wounds and/or asperities on the surface.

Thus, with the transmitted light intensity measurement unit according to the present invention, scattering and/or absorption by the air layer intermediate between the duct wall and the light-transmissive member and by the microscopical wounds and/or asperities on the surface of the duct wall almost or completely disappear, so that light attenuation due to the scattering and/or absorption can be reduced. Therefore, an enough quantity of light which is supplied from the light source, transmitted through the duct and reached to the light receiving element, can be obtained.

In addition, in the transmitted light intensity measurement unit according to the present invention, it is preferable if the light-transmissive member is a convex lens having a convex-curved surface abutting the duct wall, because the light can be converged by the convex lens so that the light is passed through the light-transmissive member and the duct wall efficiently.

Further, in the transmitted light intensity measurement unit according to the present invention, it is preferable if the convex lens is a ball lens, because the light can be converged at a part of the light-transmissive member abutting the duct wall so that the light is passed through the light-transmissive member and the duct wall more efficiently.

EMBODIMENTS FOR CARRYING OUT THE INVENTION

Figure 1A:
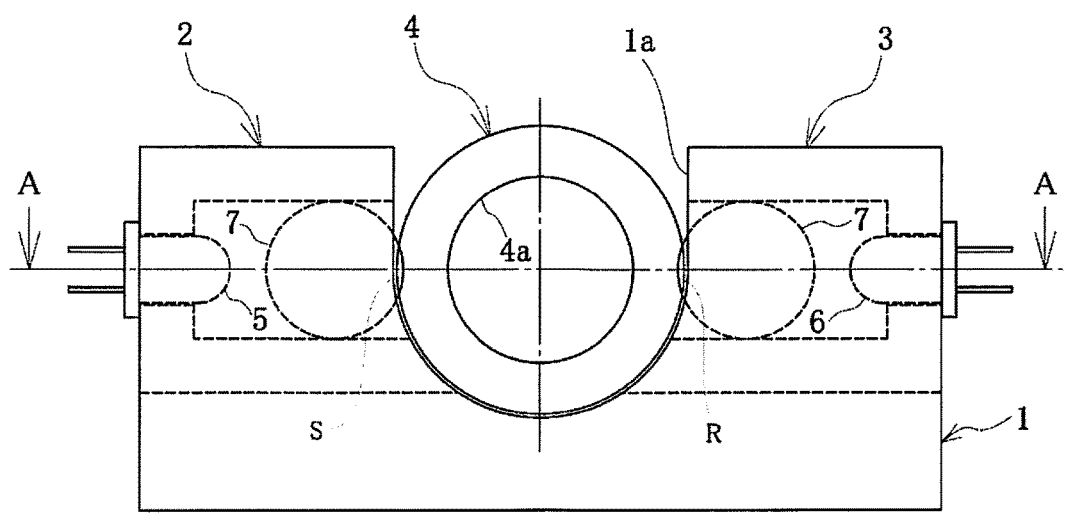
FIG. 1(a) is a front view illustrating an embodiment of the transmitted light intensity measurement unit according to the present invention.
Figure 1B:
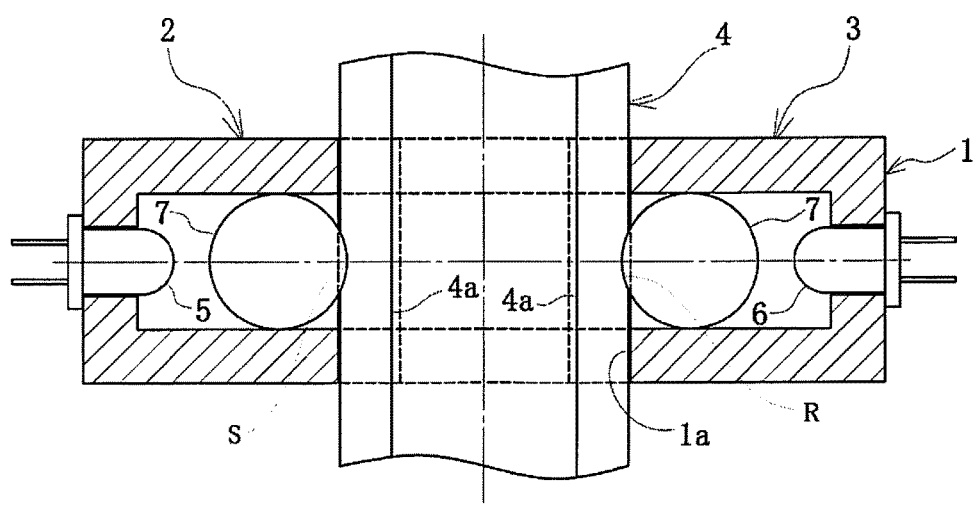
FIG. 1(b) is a cross-sectional view along the A-A line in FIG. 1(a).

In the following, embodiments of the present invention will be described in detail by way of example based on the drawings. Herein, FIG. 1(a) is a front view illustrating an embodiment of the transmitted light intensity measurement unit according to the present invention, and FIG. 1(b) is a cross-sectional view along the A-A line in FIG. 1(a).

The transmitted light intensity measurement unit of the embodiment is used in a fluid concentration measuring device which measures a concentration of a fluid flowing through a duct having a light-transmissive and deformable duct wall, based on the Beer-Lambert law, for measuring an intensity of a transmitted light passed transversely across the duct. As such a duct described above, a resin tube having a light-transmissive and deformable tube wall is well known. Further, as a fluid concentration measuring device which measures a concentration of a fluid flowing in such a duct based on the Beer-Lambert law, for example, a fluid concentration measuring device which measures a concentration of a blood flowing in a resin tube disclosed by the Patent Document 1 is known.

The transmitted light intensity measurement unit of the embodiment used in the above described fluid concentration measuring device comprises: a tube holder 1 having a U-shaped notch portion 1a upwardly opening at a central part in longitudinal direction of the tube holder 1. Further, the transmitted light intensity measurement unit of the embodiment has a light emitting unit 2 and a light receiving unit 3 respectively provided in a placement in which the light emitting unit 2 and the light receiving unit 3 are mutually opposed behind the notch portion 1a. The tube holder 1 is able to hold a resin tube 4 in the notch portion 1a, in a direction traversing the tube holder 1.

The light emitting unit 2 has a light emitting element 5 such as a light-emitting diode (LED) or a laser diode etc. which is supplied with electricity and emits light, as a light source which supplies light into the resin tube 4 from a light supply part S located on the surface of the resin tube 4. The light receiving unit 3 has a light receiving element 6, such as a photodiode or a phototransistor etc. which receives light supplied from the light supply part S and passed through inside of the tube wall 4a as a duct wall of the resin tube 4 and through a blood flowing in the resin tube 4, at a light receiving part R located on an opposite side in a diametrical direction of the resin tube 4 relative to the light supply part S, and outputs an electric signal indicating an intensity of the light.

Further, the light emitting unit 2 has a ball lens 7 as a light-transmissive member, wherein the ball lens 7 is disposed on a light path between the light emitting element 5 and the light supply part S and abuts the light supply part S in the tube wall 4a of the resin tube 4, and closely contacts the tube wall 4a by elastically dent the tube wall 4a at the light supply part S. Similarly, the light receiving unit 3 has a ball lens 7 as a light-transmissive member, wherein the ball lens 7 is disposed on a light path between the light receiving element 6 and the light receiving part R and abuts the light receiving part R in the tube wall 4a of the resin tube 4, and closely contacts the tube wall 4a by elastically dent the tube wall 4a at the light receiving part R.

Figure 2A:
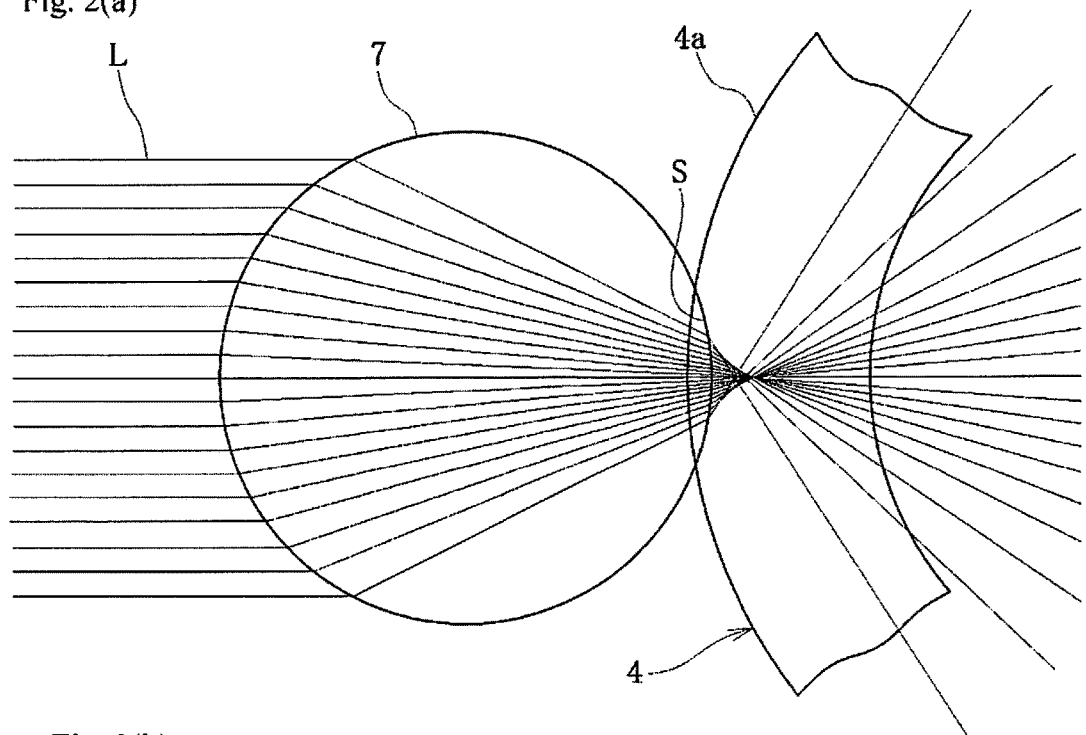
FIG. 2(a) is an explanatory diagram showing a light converging condition of a ball lens in the transmitted light intensity measurement unit of the above described embodiment.

FIG. 2(a) is an explanatory diagram showing a light converging condition of a ball lens 7 at the side of the light emitting unit 2 by deputy in the transmitted light intensity measurement unit of the embodiment. The light L in a condition of almost parallel rays emitted from the light emitting element 5 herein not shown enters in the ball lens 7 and converged to some degree. The light L passes the light supply part S in the converged thin condition and supplied in the tube wall 4a, and then further converged in the tube wall 4a of the resin tube 4. And also at the side of the light receiving unit 3, the light entered in the ball lens 7 through the light receiving part R from inside of the tube wall 4a of the resin tube 4 is converged to some degree and becomes in a condition of almost parallel rays, and then leaves the ball lens 7 and enters in to the light receiving unit 6.

Further, in the transmitted light intensity measurement unit of the embodiment, since the ball lenses 7 respectively disposed on the light path between the light emitting element 5 and the light supply part S and the light path between the light receiving element 6 and the light receiving part R closely contact the tube wall 4a, substantially no air layer intermediates between the tube walls 4a and the ball lenses 7, and surfaces of the tube walls 4a are made smooth by crushing microscopical wounds and/or asperities on the surfaces with the abutting part of the ball lenses 7.

Therefore, with the transmitted light intensity measurement unit of the embodiment, scattering and/or absorption by the air layer intermediate between the tube wall 4a and the ball lens 7 and by the asperities etc. on the surface of the tube wall 4a almost or completely disappear, so that light attenuation due to the scattering and/or absorption can be reduced. Thus, an enough quantity of light which is supplied from the light emitting element 5, transmitted through the resin tube 4 and reached to the light receiving element 6, can be obtained.

Further, with the transmitted light intensity measurement unit of the embodiment, since the light-transmissive member is a ball lens 7 which is a kind of convex lens having a convex-curved surface abutting the tube wall 4a, the light can be converged especially at a part of the ball lens 7 abutting the light supply part S and the light receiving part R of the tube wall 4a so that the light is passed through the tube wall 4a more efficiently.

When two of such the transmitted light intensity measurement unit of the embodiment having mutually different distances between the ball lens 7 of the side of the light emitting unit 2 and the ball lens 7 of the side of the light receiving unit 3 are used in the fluid concentration measuring device described in FIG. 1(a) of the Patent Document 1, as described in the Patent Document 1, the light emitted from the light emitting elements 5 in the two light emitting units 2 each driven by a light emitting element driver, pass through the tube wall 4a of the resin tube 4 respectively held between the light emitting units 2 and the light receiving units 3 of the two transmitted light intensity measurement units and compressively deformed in the diametrical direction, on the side closer to the light emitting unit 2, a blood flowing through the resin tube 4, and the tube wall 4a on the side farther away from the light emitting unit 2 (on the opposite side), i.e., on the side closer to the light receiving unit 3. Then, the light passed through the light paths having mutually different distances are received by the light receiving elements 6 in the light receiving units 3, and the light receiving elements 6 in the two light receiving units 3 output electrical signals each having a level according to the intensity of the light received.

The output signals of the light receiving elements 6 in the two light receiving units 3 are, for example, each amplified by an amplifier, removed high-frequency noise components thereof by a low-pass filter, converted by an analog-digital converter (A/D) from an analog signal into a digital signal, and input into a central processing unit (CPU). The CPU controls the operation of the light emitting element driver, and preferably selectively makes the light emitting units 2 emit light so as to avoid interference between the two light emitting units 2. In addition, the CPU obtains a concentration of the blood inside the resin tube 4 by the known way, from the output signals of the light receiving elements 6 at the respective light path distances, in which, from the light intensity in case of receiving at the light receiving part R the light from the light supply part S over each of the light path distances, the CPU obtains a plurality of relational expressions based on the Beer-Lambert law, and further obtains a concentration of the blood in the resin tube 4 from the light intensity at either of the light receiving elements 6 based on the relational expressions for the plurality of light path distances and outputs a signal indicating data on the concentration.

Therefore, with the fluid concentration measuring device using the transmitted light intensity measurement units of the embodiment, since an enough quantity of light which is supplied from the light emitting element 5, transmitted through the resin tube 4 and reached to the light receiving element 6, can be obtained, a measuring accuracy of the concentration of the blood can be increased by comparison to conventional devices.

Figure 2B:
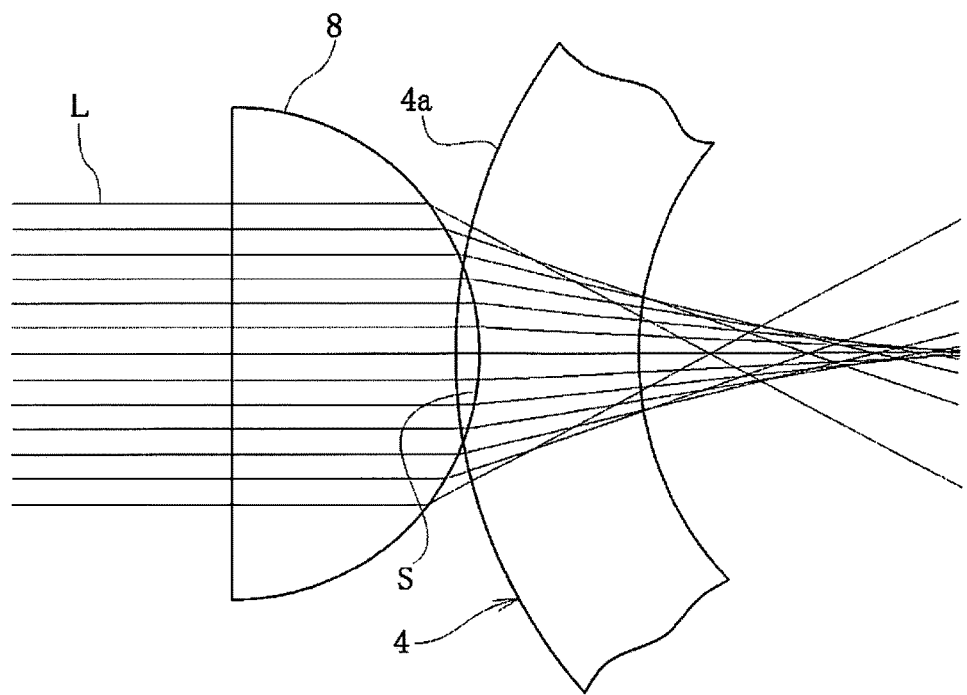
FIG. 2(b) is an explanatory diagram showing a light converging condition of a hemispherical lens in another embodiment of the transmitted light intensity measurement unit according to the present invention.

FIG. 2(b) is an explanatory diagram showing a light converging condition of a hemispherical lens in another embodiment of the transmitted light intensity measurement unit according to the present invention. In the transmitted light intensity measurement unit of the embodiment, instead of the ball lenses 7 in the former embodiment, hemispherical lenses 8 are used as the light-transmissive member of the light emitting unit 2 and the light receiving unit 3. Spherical surfaces of the hemispherical lenses 8 abut the light supply part S and the light receiving part R and closely contact the tube wall 4a by elastically dent the tube wall 4a at the light supply part S and the light receiving part R.

With the transmitted light intensity measurement unit of the embodiment, an enough quantity of light which is supplied from the light emitting element 5, transmitted through the resin tube 4 and reached to the light receiving element 6, can be obtained, while the quantity of light is less than that of the former embodiment.

Though the embodiments have been described based on the examples shown in the drawings, the present invention is not limited to the embodiments described above, but can be appropriately modified within the scope of claims. For example, in the transmitted light intensity measurement units of the above embodiments, as the light-transmissive member, the ball lenses 7 and the hemispherical lenses 8 are provided to both of the light emitting unit 2 and the light receiving units 3. Instead, the light-transmissive member may be provided to either side, especially provided to only the side of the light emitting unit 2. In this case, the light-transmissive member at the side of the light receiving unit 3 may abut the tube wall 4a of the resin tube 4 with a flat surface.

Further, in the above described example of the fluid concentration measuring device using the transmitted light intensity measurement units of the embodiment, a concentration of a blood as a liquid is measured. Instead, the fluid concentration measuring device may be used for measuring another kind of liquid. In this case, as the light supplied from the light source, selecting a light of a wavelength having higher absorptive rate is preferable, because difference of the light intensity at the light receiving part becomes clearer according to the thickness of the duct wall etc.

Further, in the above described example of the fluid concentration measuring device, light is supplied respectively from the light supply parts with regard to the two light path distances, and the intensity of the light are obtained by receiving the light at the light receiving parts. Instead, three or more of light path distances may be set and the light intensity at each of the light receiving parts may be obtained. With this constitution, the measurement precision can be further enhanced, for example, by averaging the results obtained from the light path distances.

INDUSTRIAL APPLICABILITY

Thus, with the transmitted light intensity measurement unit according to the present invention, scattering and/or absorption by the air layer intermediate between the duct wall and the light-transmissive member and by the asperities etc. on the surface of the duct wall almost or completely disappear, so that light attenuation due to the scattering and/or absorption can be reduced. Therefore, an enough quantity of light which is supplied from the light source, transmitted through the duct and reached to the light receiving element, can be obtained.

DESCRIPTION OF REFERENCE SYMBOLS

1 Tube holder
1a Notch portion
2 Light emitting unit
3 Light receiving unit
4 Resin tube
4a Tube wall
5 Light emitting element
6 Light receiving element 7 Ball lens
8 Hemispherical lens
L Light

The invention claimed is:

1. A transmitted light intensity measurement unit used in a fluid concentration measuring device which measures a concentration of a fluid flowing through a duct having a light-transmissive and deformable duct wall, the transmitted light intensity measurement unit comprising:
   a light source for supplying light into the duct from a light supply part on a surface of the duct;
   a light receiving element for receiving the light, which has been passed from the light supply part through the duct wall and the fluid inside the duct, at a light receiving part located on an opposite side in a diametrical direction of the duct relative to the light supply part, the light receiving element configured to output a signal indicating an intensity of the light; and
   a light-transmissive member disposed on at least one light path among a light pass between the light source and the light supply part and a light pass between the light receiving element and the light receiving part, the light-transmissive member being a convex lens having a convex-curved surface configured to elastically deform the duct wall by abutting and closely contacting the duct wall.

2. The transmitted light intensity measurement unit according to claim 1, wherein the convex lens is a ball lens.

3. The transmitted light intensity measurement unit according to claim 1, wherein the duct having the light-transmissive and deformable duct wall is a resin tube.

4. The transmitted light intensity measurement unit according to claim 2, wherein the duct having the light-transmissive and deformable duct wall is a resin tube.

5. The transmitted light intensity measurement unit according to claim 1, wherein the convex lens is configured to converge light at the light supply part and/or at the light receiving part such that the light is efficiently passed through the deformed duct wall.

6. The transmitted light intensity measurement unit according to claim 1, wherein the entire convex-curved surface configured to elastically deform the duct wall is transmissive to light.

* * * * *